(12) United States Patent
Williams et al.

(10) Patent No.: US 8,413,313 B2
(45) Date of Patent: Apr. 9, 2013

(54) DIVIDED-END ARTIFICIAL LIMB

(76) Inventors: David Delon Williams, Provo, UT (US);
William G. Pitt, Orem, UT (US); Peter Austin Jepsen, Provo, UT (US);
Douglas Turley Wright, Provo, UT (US); Carl Jay Ellingson, Provo, UT (US); Daniel August Susumu Marler, Atlanta, GA (US)

(*) Notice: Subject to any disclaimer, the term of this patent is extended or adjusted under 35 U.S.C. 154(b) by 298 days.

(21) Appl. No.: 12/940,909

(22) Filed: Nov. 5, 2010

(65) Prior Publication Data
US 2011/0107581 A1 May 12, 2011

Related U.S. Application Data

(60) Provisional application No. 61/280,601, filed on Nov. 6, 2009, provisional application No. 61/339,050, filed on Mar. 1, 2010.

(51) Int. Cl.
*A61F 2/66* (2006.01)
*A61F 1/00* (2006.01)

(52) U.S. Cl.
USPC ...... 29/525.01; 29/447; 29/525.02; 29/527.1; 29/412; 29/417; 623/52; 623/55; 264/138; 264/294

(58) Field of Classification Search .......... 29/447, 29/525.01, 525.02, 527.1, 412, 414; 623/52, 623/55; 264/138, 294
See application file for complete search history.

(56) References Cited

U.S. PATENT DOCUMENTS

| | | | |
|---|---|---|---|
| 4,306,320 A | 12/1981 | Delp | |
| 4,446,580 A | 5/1984 | Furuya | |
| 4,459,709 A | 7/1984 | Leal | |
| 4,547,913 A * | 10/1985 | Phillips | 623/27 |
| 4,822,363 A * | 4/1989 | Phillips | 623/27 |
| 4,959,073 A * | 9/1990 | Merlette | 623/55 |
| 5,037,444 A | 8/1991 | Phillips | |
| 5,181,933 A | 1/1993 | Phillips | |
| 5,217,500 A | 6/1993 | Phillips | |
| 5,258,039 A | 11/1993 | Goh | |
| 5,509,936 A * | 4/1996 | Rappoport et al. | 623/27 |
| 5,571,207 A | 11/1996 | Houser | |
| 5,653,768 A * | 8/1997 | Kania | 623/55 |
| 5,695,527 A | 12/1997 | Allen | |
| 5,725,598 A | 3/1998 | Phillips | |
| 6,053,946 A | 4/2000 | Wilkinson | |
| 6,241,776 B1 * | 6/2001 | Christensen | 623/52 |
| 6,398,818 B1 * | 6/2002 | Merlette et al. | 623/55 |
| 6,719,807 B2 | 4/2004 | Harris | |

(Continued)

*Primary Examiner* — Peter DungBa Vo
*Assistant Examiner* — Anthony Green
(74) *Attorney, Agent, or Firm* — Richard C. Gelati, Esq.

(57) ABSTRACT

The present invention provides divided-end artificial limbs and methods for making divided-end artificial limbs that are inexpensive, simple, and customizable. A limb is formed by dividing an end of an elongated shaft member into extending prongs that are shaped into custom lengths and curvatures. Furthermore, the method of the present invention provides affixing a sole plate to the limb, reinforcement of the prongs by nesting additional prongs within the elongated shaft member, dividing the proximal end of the shaft member into circumferentially spaced-apart fingers, and dividing a midsection of the shaft member into circumferentially spaced-apart flexing vanes. The present invention also provides that the prongs may be further modified by division into toe and heel extensions or by wrapping a prong around another prong to form a sole. Methods of reducing stress concentration using bolts and stress relief holes in these limbs are also presented.

15 Claims, 14 Drawing Sheets

U.S. PATENT DOCUMENTS

| | | |
|---|---|---|
| 7,044,984 B2 | 5/2006 | Kuiken |
| 7,060,104 B2 * | 6/2006 | Phillips .......................... 623/55 |
| 7,618,464 B2 * | 11/2009 | Christensen .................... 623/55 |
| 7,749,423 B2 * | 7/2010 | Bader .......................... 264/511 |
| 8,034,121 B2 * | 10/2011 | Christensen .................... 623/55 |
| 2002/0133237 A1 * | 9/2002 | Christesen ...................... 623/24 |
| 2003/0120354 A1 * | 6/2003 | Doddroe et al. ................. 623/55 |
| 2005/0171618 A1 * | 8/2005 | Christensen .................... 623/56 |

* cited by examiner

DIVIDED-END ARTIFICIAL LIMB

CROSS-REFERENCE TO RELATED APPLICATIONS

Priority is claimed under 35 U.S.C. §119(e) and 17 C.F.R. §1.78(a) for the following prior-filed U.S. provisional patent applications: (1) application number U.S. 61/280,601, with a filing date of Nov. 6, 2009, and (2) application number U.S. 61/339,050, with a filing date of Mar. 1, 2010.

BACKGROUND OF THE INVENTION

1. The Field of the Invention

The present invention relates to artificial limbs for disabled persons, and to methods for making artificial limbs.

2. The Relevant Technology

Advances in the field of artificial limbs have given rise to a great number of prosthetic solutions for amputees and other disabled persons. These persons need durable, comfortable, and lifelike prosthetics to carry out everyday tasks and lead normal lives. In developing nations, especially those afflicted by prolonged warfare, there is a widespread need for these prosthetics, but they are often far too expensive to be a realistic solution for those with little disposable income. Modern prosthetic legs and feet use compliant mechanisms and other designs made of advanced materials that often must be custom made for the wearer by a skilled prosthetist. These factors magnify the cost of production and maintenance of the prosthesis. They may also have multiple complex parts and mechanisms that can be difficult to adjust to fit the user's needs.

It would therefore be an advantage to have a method to make a relatively inexpensive, comfortable, and effective prosthetic device which can be made, used, and maintained by amputees, or which can be provided to them in a more affordable manner. It would be even further advantage to have a prosthetic device with a minimal number of parts and could be made from a wide range of available materials so that unskilled manufacturers would not find it prohibitively difficult to build and understand its operation. Such a device would also be advantageously adaptable to attach to limbs of varying size, shape, and sensitivity and able to be customized to simulate the natural motion of a wearer's limb.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

The embodiments described below and in the claims relate to divided-end artificial limbs and methods for making divided-end artificial limbs. These devices are generally useful as prostheses for legs and feet, and the methods claimed hereinafter are directed to an improved method of making such prosthetic devices that can be implemented relatively inexpensively, even in conditions of scarce resources. Several of the claimed methods also provide a simple means of adjusting the size and shape of a prosthesis to custom-fit to the wearer's wishes, even after the prosthesis is manufactured.

In some embodiments, an artificial limb is made by a method wherein an elongated shaft member is divided on a distal end into anterior and posterior portions to form respective anterior and posterior prongs. Those prongs are shaped to predefined lengths and curvatures based on the size and features of the amputee. This artificial limb may then be attached to the residual limb of an amputee for use as a prosthesis.

In some embodiments, such as when the limb is constructed from PVC or other materials with high strength to modulus ratio and low friction, a beneficial shaping method comprises heating the anterior and posterior prongs, and cutting or molding the prongs to a desired length. Using this technique, the prosthetic may be readily and inexpensively customized in shape and size to fit in an amputee's shoes, allowing the amputee to save the cost of acquiring new clothing to fit the artificial limb.

In some embodiments, the elongated shaft member is a tubular member, and in some of those embodiments, that member is made of plastic or fibrous composite in order to serve the needs of the amputee.

In some embodiments, the proximal end of the elongated shaft member is divided and shaped into a plurality of circumferentially spaced-apart fingers in an enlarged cup shape suitable for reception of the amputee's residual limb. This may be useful for attaching the artificial limb to the amputee's residual limb because it surrounds the residual limb with the artificial limb, which can then be wrapped tightly against, tied to, or otherwise connected to the residual limb at more points.

In some embodiments, a portion of the elongated shaft member between the proximal and distal ends of the member is divided in a longitudinal direction and shaped to form a plurality of circumferentially spaced-apart vanes that flex outward from the member's longitudinal shaft when a longitudinal load is applied to the member. Typically, this step is used when more shock absorption is required in the artificial limb, because when the artificial limb is made with compliant materials, the vanes will elastically deform under the longitudinal load and provide a restorative force to the amputee's steps as she places her weight on the artificial limb.

In some embodiments, a bolt is attached through the anterior prong and the posterior prong such that the attachment of the bolt limits the maximum movement of those prongs when they flex away from the longitudinal axis of the elongated shaft member. This bolt may also be beneficially attached in this manner to reduce stresses and cracking in the shaft material.

In some embodiments, the anterior side and posterior side of the distal end of the elongated shaft member are divided by a slit in the shaft member that terminates in a hole through the shaft member. The hole has a larger diameter than the width of the slit, such that the hole is capable of reducing stress concentration in the hole end of the slit when the anterior prong and posterior prongs are drawn apart from each other.

In some embodiments, the anterior prong is divided into a plurality of toe extensions that are independently flexible with respect to the remainder of the artificial limb. In some embodiments, the posterior prong is divided into a plurality of heel extensions that are independently flexible with respect to the remainder of the artificial limb. The divisions of the prongs in these embodiments can in some cases be formed by cutting, cracking, or molding the prongs so that the toe and heel extensions have a desired length and rigidity.

In some embodiments, a sole plate is affixed to the anterior prong and the posterior prong. This sole plate can benefit the amputee by providing a more natural foot shape and may reduce wear and improve fit of the limb in shoes. A person practicing the invention in this fashion may find it useful to mold an arch in the sole plate to more closely resemble the amputee's natural foot shape. The sole plate may be affixed using solvents, glues, mechanical fasteners, or other methods that would provide a strong link between the prongs and the sole plate.

In some embodiments, a step is included of reinforcing the anterior and posterior prongs of the distal end of the elongated shaft member by dividing the distal end of an additional elongated shaft member into anterior and posterior prongs and attaching the additional elongated shaft member to the distal end of the elongated shaft member such that the prongs and the additional prongs are nested to create a reinforced anterior prong and an reinforced posterior prong. Several layers of additional prongs can be nested in this fashion to make the original prongs more rigid and less likely to break under a load. The additional nested prongs can provide more safety for the amputee as well, because the additional prongs may act as a backup support for the wearer in case the other prongs fail.

In some embodiments, an outer elongated shaft member and an inner elongated shaft member are used to make an artificial limb. The distal end of the inner elongated shaft member is divided into an inner anterior prong and an inner posterior prong extending in anterior and posterior directions from an inner longitudinal axis of the inner elongated shaft member. The distal end of the outer elongated shaft member is also divided into an outer anterior prong and an outer posterior prong. The inner elongated shaft member is then nested with the outer elongated shaft member so that the anterior side of each elongated shaft member are aligned, and the outer anterior prong and outer posterior prong are shaped to distally wrap around the inner anterior prong and the inner posterior prong. Among other benefits, this wrap-around method of producing the artificial limb can reduce or eliminate the need for a sole plate to be attached to the limb, can result in a more rugged foot than other methods, and can reduce the need for extra layers of reinforcing nested shaft material.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
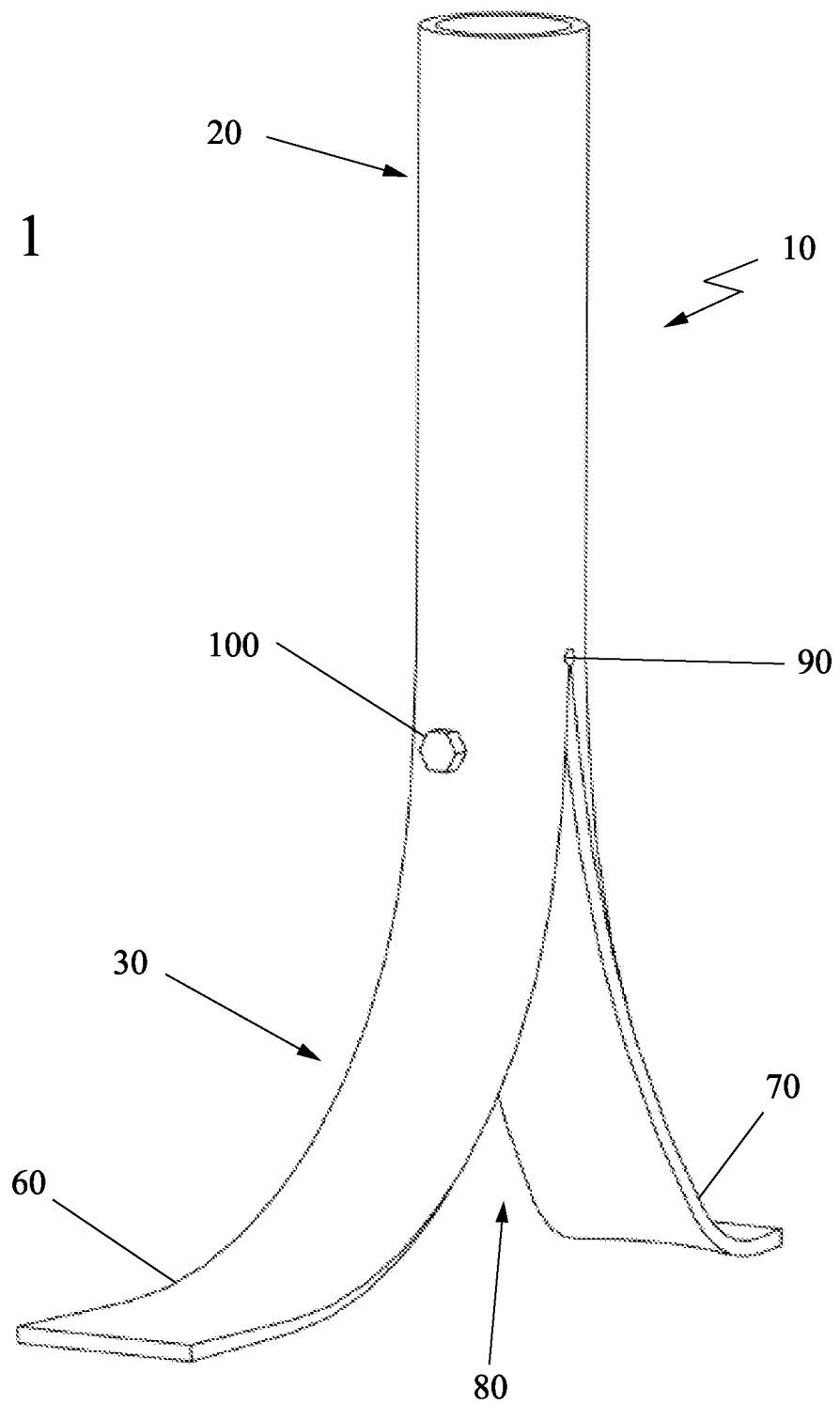
FIG. 1 illustrates a perspective view of an artificial limb of the present invention.

Referring to the drawings in detail, the elongated shaft member 10 is shown generally in the drawings after it has been divided and shaped according to the methods of the claims. The elongated shaft member 10 may take various geometries and cross-sectional shapes, including tubular shape, rectangular, hexagonal, or other polygonal cross-sectional prism, so long as the remaining steps of the claimed methods can be performed. The length of the elongated shaft member 10 as measured along a longitudinal axis from its proximal end 20 to its distal end 30 should be sufficient to span the distance from an attachment point at the device wearer's residual limb to the ground after the limb is manufactured. The elongated shaft member may be made of any material with a high strength to modulus ratio and low friction, and materials including but not limited to ABS, acrylic, acetal copolymer, butyrate, carbon fiber, delrin, garolite, nylon, PETG, polycarbonate, polyethylene (HDPE), PTFE, PVC, polyethylene terephthalate (PET), polyimide, polypropylene, polystyrene, and teflon.

The elongated shaft member 10 has an anterior side 40 and a posterior side 50. When practicing the invention, these sides are not required to correspond with the anterior and posterior directions relative to the body of the amputee. The "anterior" and "posterior" directional descriptions herein are referenced in this manner to provide convenience in description and visualization, but they could also be synonymously referred to as generic "first" and "second" directions to the extent that the invention may still be practiced after such a modification. The anterior 40 and posterior 50 sides are positioned on different parts of the elongated shaft member 10 such that when these sides are divided, the elongated shaft member's distal end 30 forms an anterior prong 60 corresponding to the anterior side 40 and a posterior prong 70 corresponding to the posterior side 50. The anterior prong 60 and posterior prong 70 extend in the anterior and posterior directions from the longitudinal axis of the elongated shaft member, respectively, after being shaped to a length and curvature based on the size and features of the wearer.

The division of the anterior side 40 and posterior side 50 may be performed by cutting a slit 80 in the distal end 30 of the elongated shaft member 10 between its anterior side 40 and posterior side 50. The slit 80 is not required to be equidistant from the sides 40 and 50, and its location in the distal end 30 may be adjusted to provide a thicker or thinner anterior prong 60 and posterior prong 70 during manufacture of the artificial limb. The slit 80 may also be created by methods other than cutting, such as cracking or molding the distal end 30 of the elongated shaft member 10, so long as the anterior prong 60 and posterior prong 70 can be separated to the manufacturer's and wearer's needs.

In some embodiments, a stress relief hole 90 may be drilled or otherwise formed at the base of the slit 80 to reduce stresses generated in the elongated shaft member 10 when the prongs 60 and 70 flex under a load. The stress relief hole 90 should be of sufficient size in relation to the width of the slit 80 to minimize stresses when the prongs are shaped and drawn apart whenever the artificial limb is used.

Figure 2:
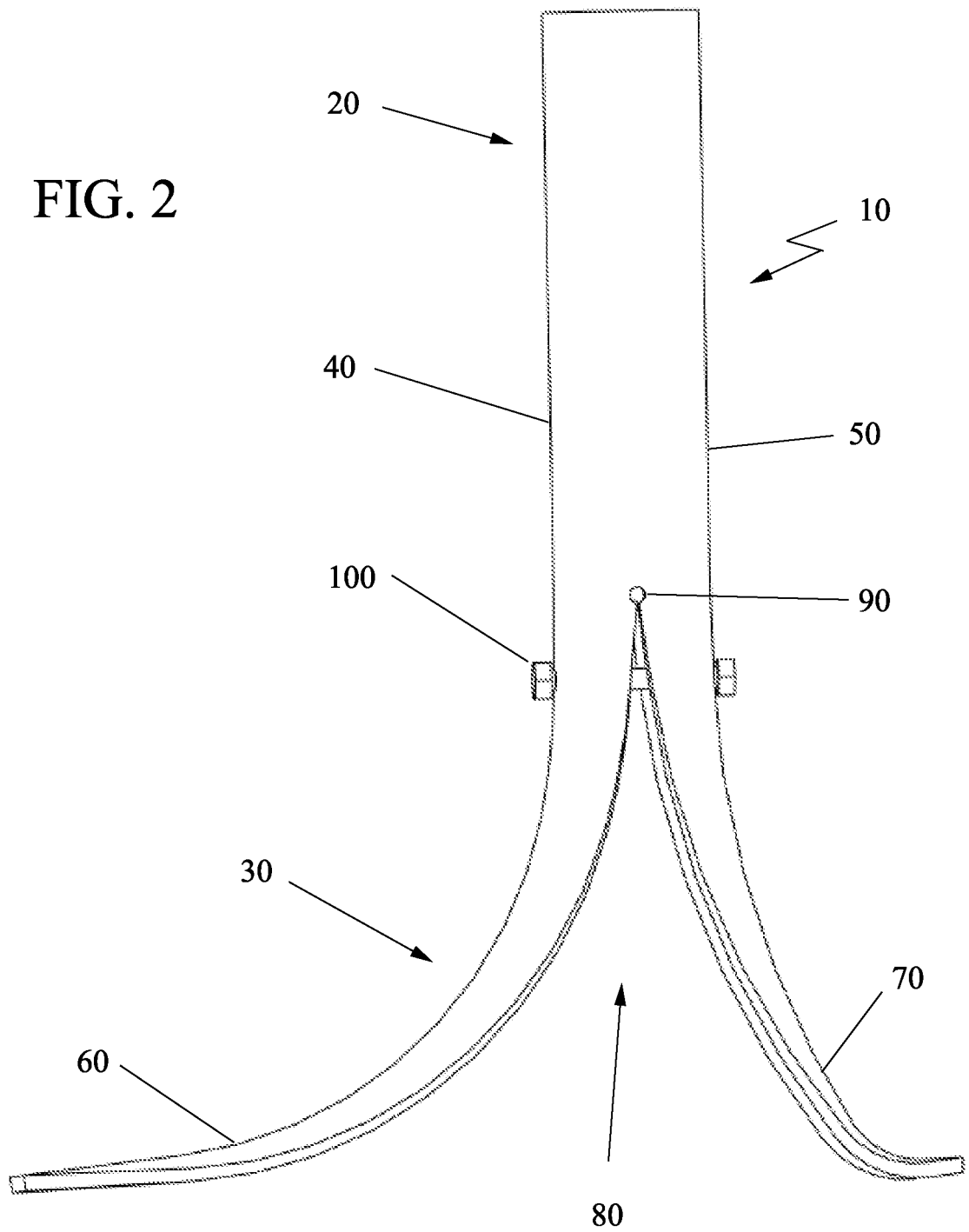
FIG. 2 illustrates a side plan view of an artificial limb of the present invention.

In some embodiments, a bolt 100 is placed through the prongs 60 and 70 and the anterior and posterior sides 40 and 50. The bolt 100 should be positioned distally from the base of the slit 80 so that when the prongs 60 and 70 are drawn apart, the bolt will limit their lateral movement. This way, the bolt 100 reduces stresses in the slit 80 by redistributing the stress that would be borne by the material at the base of the slit to the anterior and posterior sides 40 and 50 of the elongated shaft member 10 as well. It should be noted that the bolt 100 in FIGS. 1 and 2, among others, is merely illustrative in shape. The length, diameter, and end shapes of the bolt may be varied to adjust its positioning, the stress concentration reduction produced, and other design considerations. A threaded nut and bolt, for example, can be used to secure the prongs 60 and 70, but a welded metal or plastic rod that performs the same function as the bolt in that position can be suitably substituted in place of the nut and bolt.

In some embodiments the shaping of the anterior prong 60 and posterior prong 70 may be performed by heating and manually forming each prong 60 and 70 to a desired length and curvature. This is possible with an elongated shaft member made of PVC, for example, because PVC softens and becomes more malleable at elevated temperatures. Using this shaping method, the prongs 60 and 70 are heated using a heat gun, hot liquid, oven, or other heat source to reach desired softness, then they are bent outward from the longitudinal axis of the elongated shaft member until the tips of the prongs 60 and 70 are at a desired distance apart.

When the tips of the prongs 60 and 70 are positioned at a desired distance, the curvature of the prongs may also need to be adjusted to provide proper support and flexibility to the artificial limb. If the curvature of the prongs 60 and 70 is too great, the prongs may be shortened by cutting, molding, or other similar methods, and then repositioned to the desired distance apart to reduce their curvature. If the curvature of the prongs is too low, the prongs 60 and 70 may be lengthened by increasing the length of the slit 80 in the elongated support member 10. The curvature of the prongs is thereby increased when the tips of the prongs are repositioned to the original desired distance apart. Other methods of shaping to reach a desired length may include incorporating an arch into one or both prongs to shorten them, folding the tip of a prong back over itself to shorten the prong, heating and stretching the shaft material to lengthen the prong, and attaching additional material to the end of the prong to lengthen the prong. These shaping methods may also be used to widen or narrow the shape of the prongs.

Figure 3:
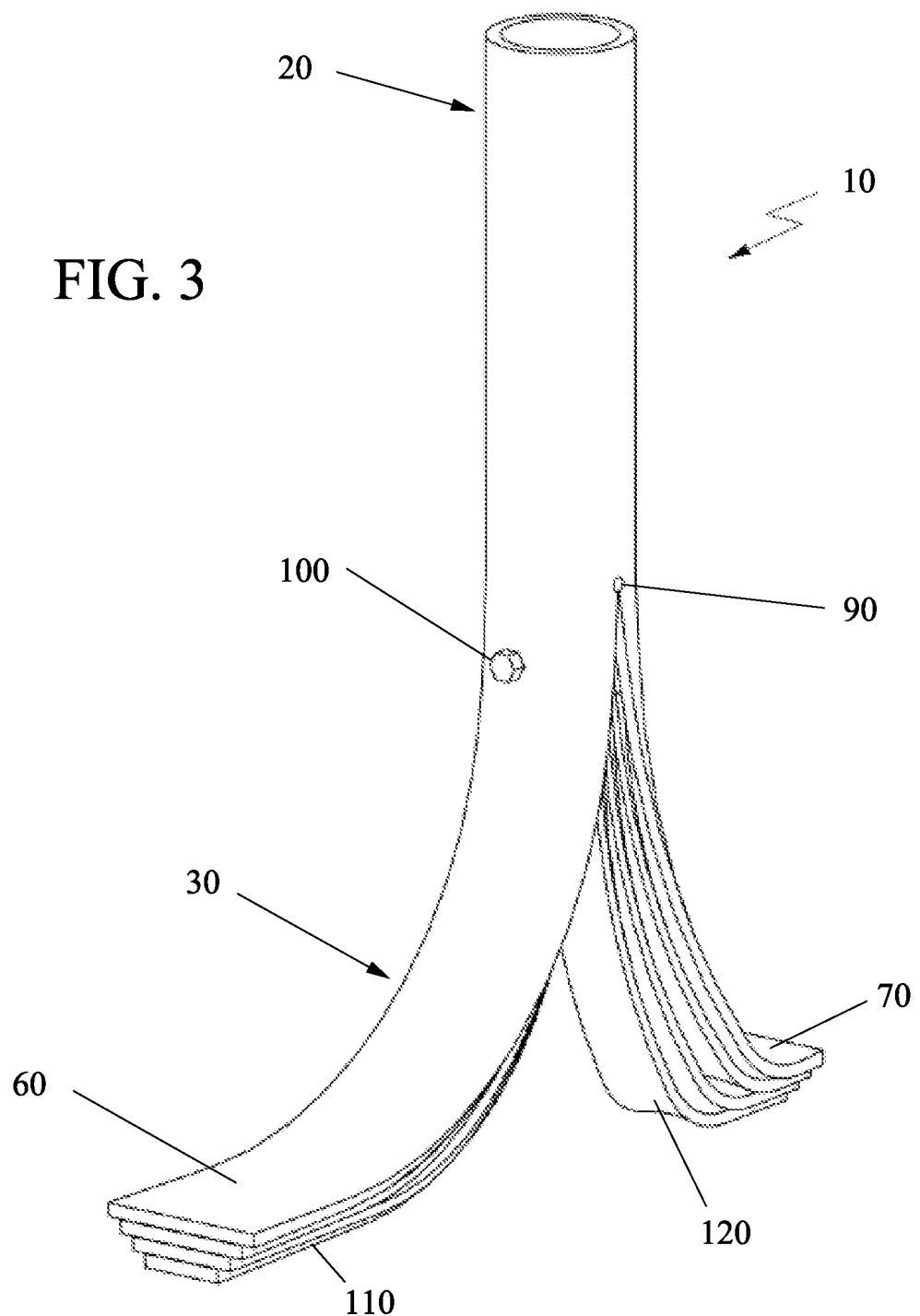
FIG. 3 illustrates a perspective view of an artificial limb of the present invention with nested reinforcement.
Figure 4:
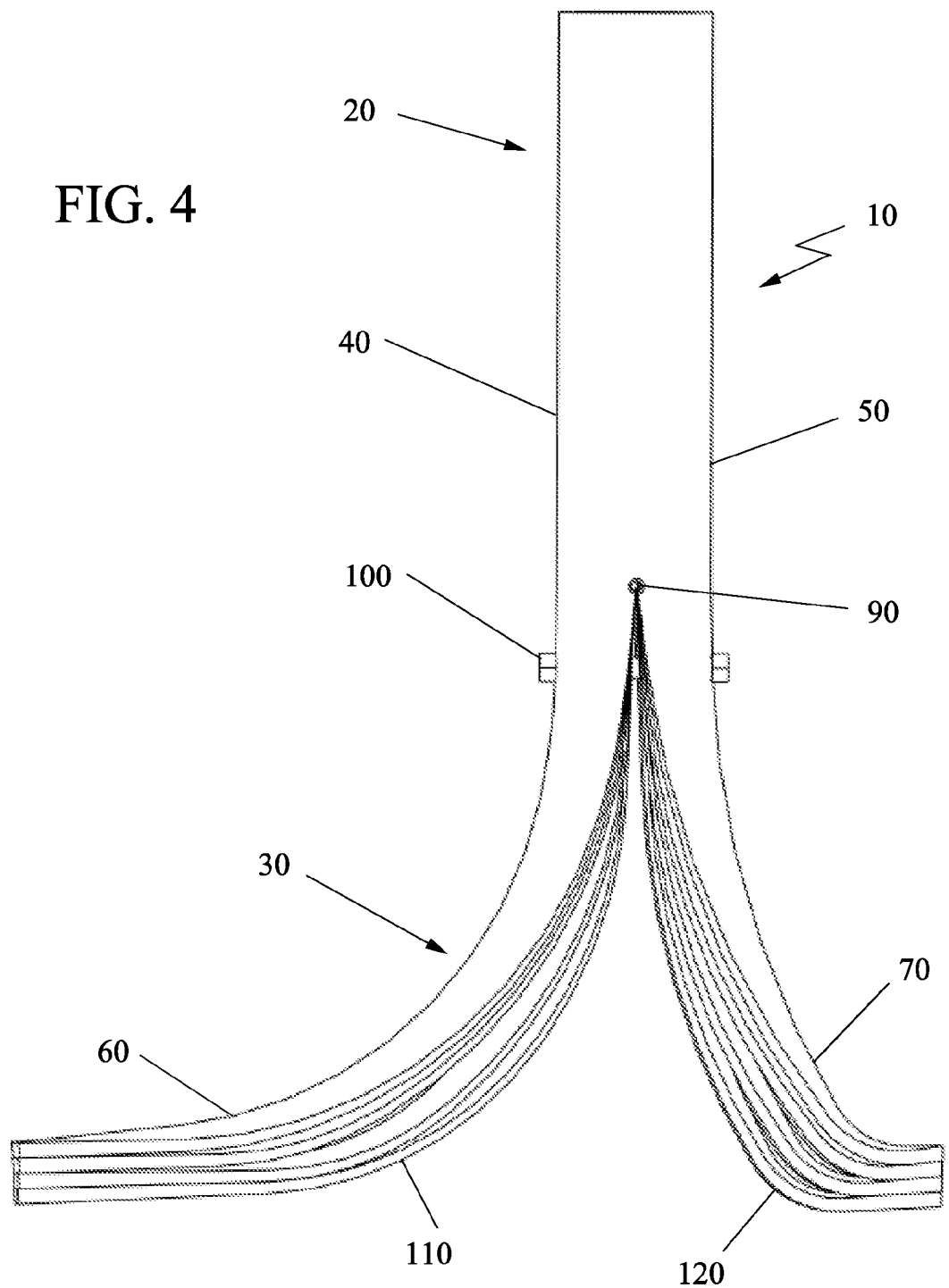
FIG. 4 illustrates a side plan view of an artificial limb of the present invention with nested reinforcement.

When shaping the prongs 60 and 70, other considerations may be necessary depending on the application in which the artificial limb will be used. If it will be used inside a shoe, the shaping step would beneficially include a procedure of rounding the corners on the tips of the prongs 60 and 70 to reduce wear to the shoe. Similarly, if a sole plate will be attached to the prongs, as depicted for example in FIG. 9, the shaping step would beneficially include molding the ends of the prongs to provide a surface that is easier to reliably connect to the sole plate, such as molding into a flat surface. If nested reinforcement prongs are incorporated into the design, as depicted for example in FIG. 3, the prongs 60 and 70 may be desirably shaped to be broader or narrower to a certain width.

In some embodiments, the shaping method differs based on the material of the elongated shaft member 10. If fibrous composite is used, it is desirable to mold the prongs to meet desired dimensions without cutting the composite material to minimize weaknesses when the prongs 60 and 70 flex under use. However, the artificial limb may still operate if composite materials are cut instead of molded. If metal shaft material is used, the shaping step may be performed by cutting, molding, bending, annealing, or forming the prongs by other comparable methods. If plastic shaft material is used, molding and cutting are examples of acceptable ways of performing the shaping step.

Figure 5:
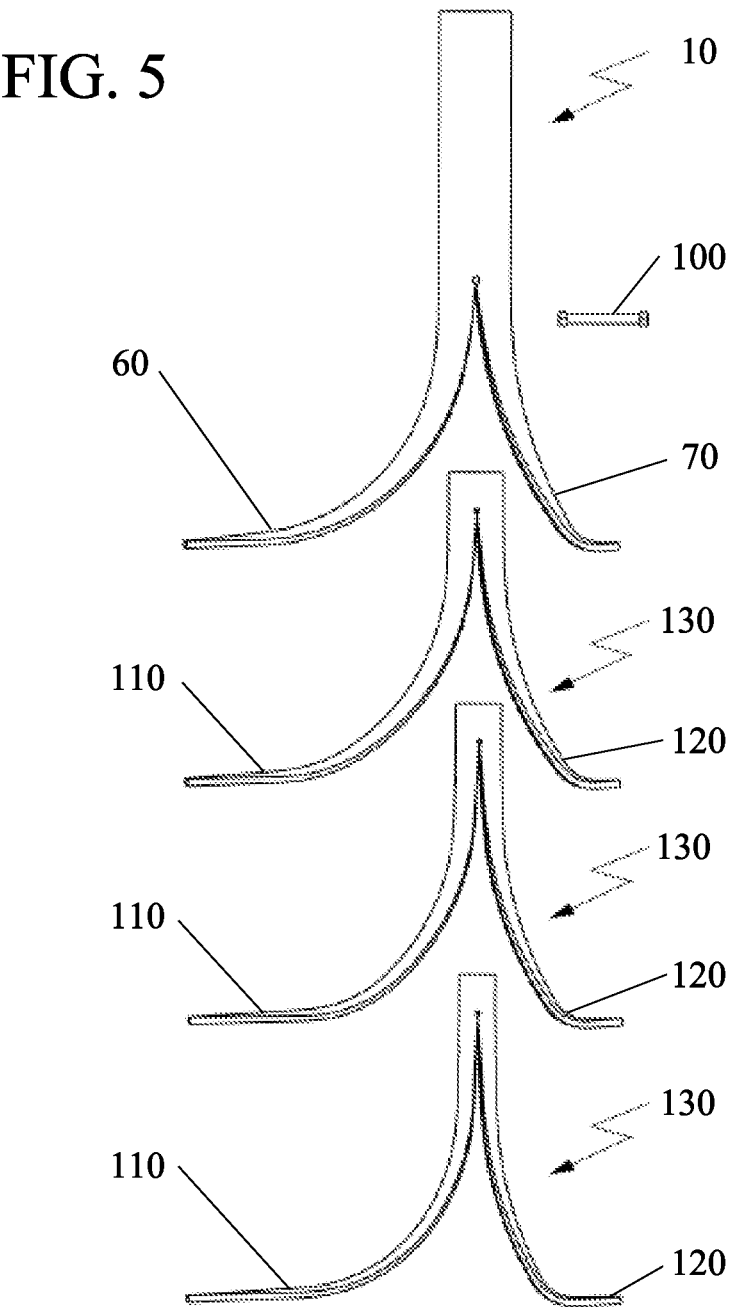
FIG. 5 illustrates a side plan exploded view of an artificial limb of the present invention with nested reinforcement.
Figure 6:
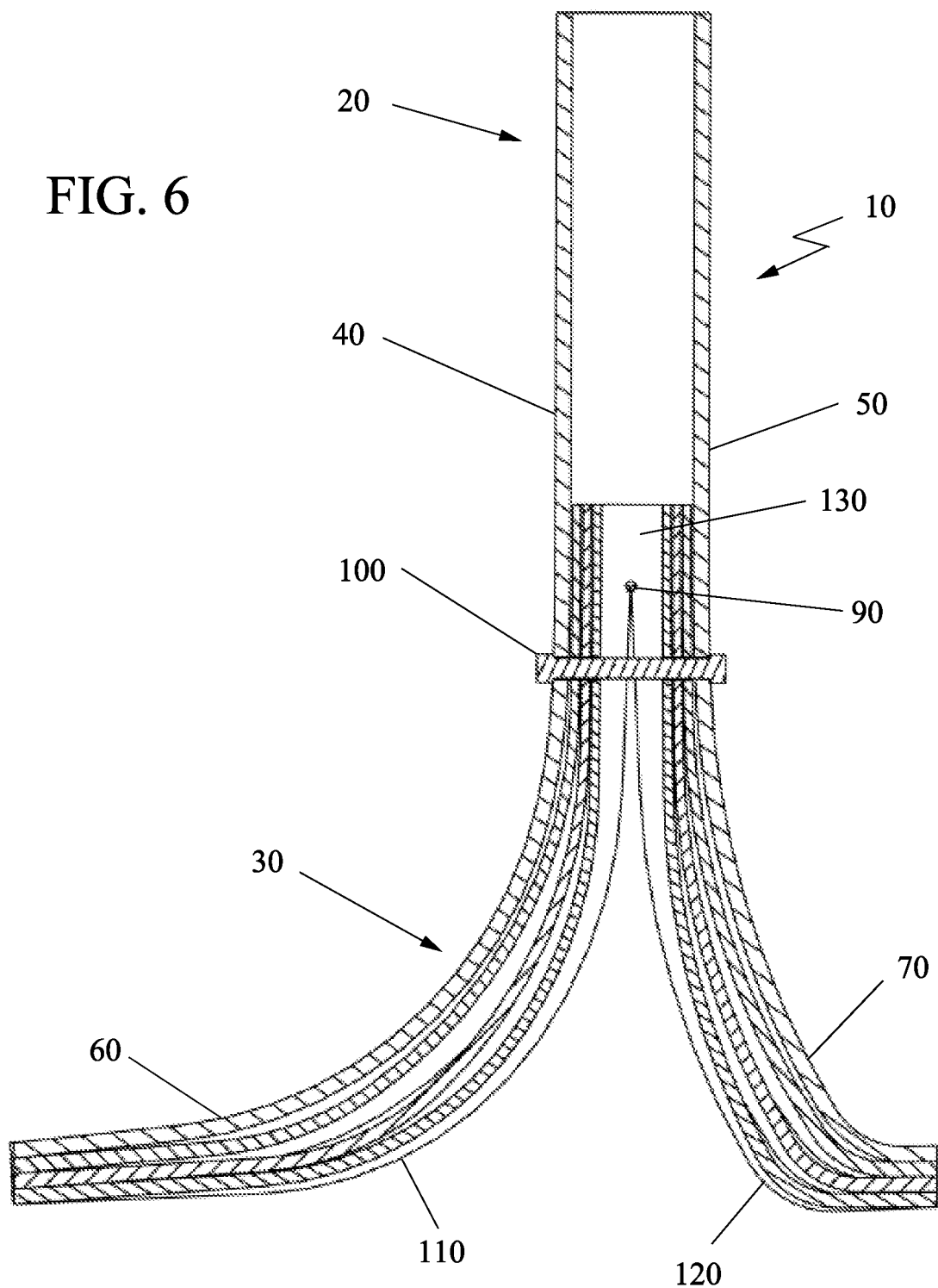
FIG. 6 illustrates a side sectional view of an artificial limb of the present invention with nested reinforcement.

In FIGS. 3, 4, 5, and 6, an artificial limb with nested reinforcement is depicted. The method of creating this type of limb follows the pattern set by the above mentioned artificial limbs, where an elongated shaft member 10 is divided at a distal end 30 into anterior and posterior prongs 60 and 70. Those prongs 60 and 70 are then reinforced by attachment of additional elongated shaft members 130 with associated reinforcing prongs 110 and 120. As shown in FIG. 5, to form the additional prongs 110 and 120, an additional elongated shaft member 130 is divided in the manner of the original elongated shaft member 10. The additional shaft member 130 is then installed in the original elongated shaft member 10 so that the prongs 110 and 120 are nested within the original prongs 60 and 70. The additional elongated shaft member 130 may also be installed on the outside of the original elongated shaft member 10 to reinforce the prongs 60 and 70. In these figures, the additional elongated shaft member 130 is shorter than the original elongated shaft member 10 at its proximal end, but the additional elongated shaft member may also be designed to be longer. A plurality of nested additional elongated shaft members 130 and prongs 110 and 120 is contemplated in this reinforcement pattern, such that the stiffness and size of the prongs 60, 70, 110, and 120 may be customized for the wearer based on the number of additional prongs 110 and 120 and their shape and materials used in their construction. The additional prongs 110 and 120 may be attached solely by the attachment of the additional elongated shaft member 130 to the elongated shaft member 10, and the additional prongs 110 and 120 may also be attached to the original prongs 60 and 70 by adhesive, solvent, welding, mechanical fasteners, or other similar means of providing a strong connection between the parts at the points of attachment. The reinforced limb may also incorporate a bolt 100 through the prongs 60, 70, 110, and 120 and stress relief hole 90 to reduce stresses in the elongated shaft members 10 and 130.

Figure 7:
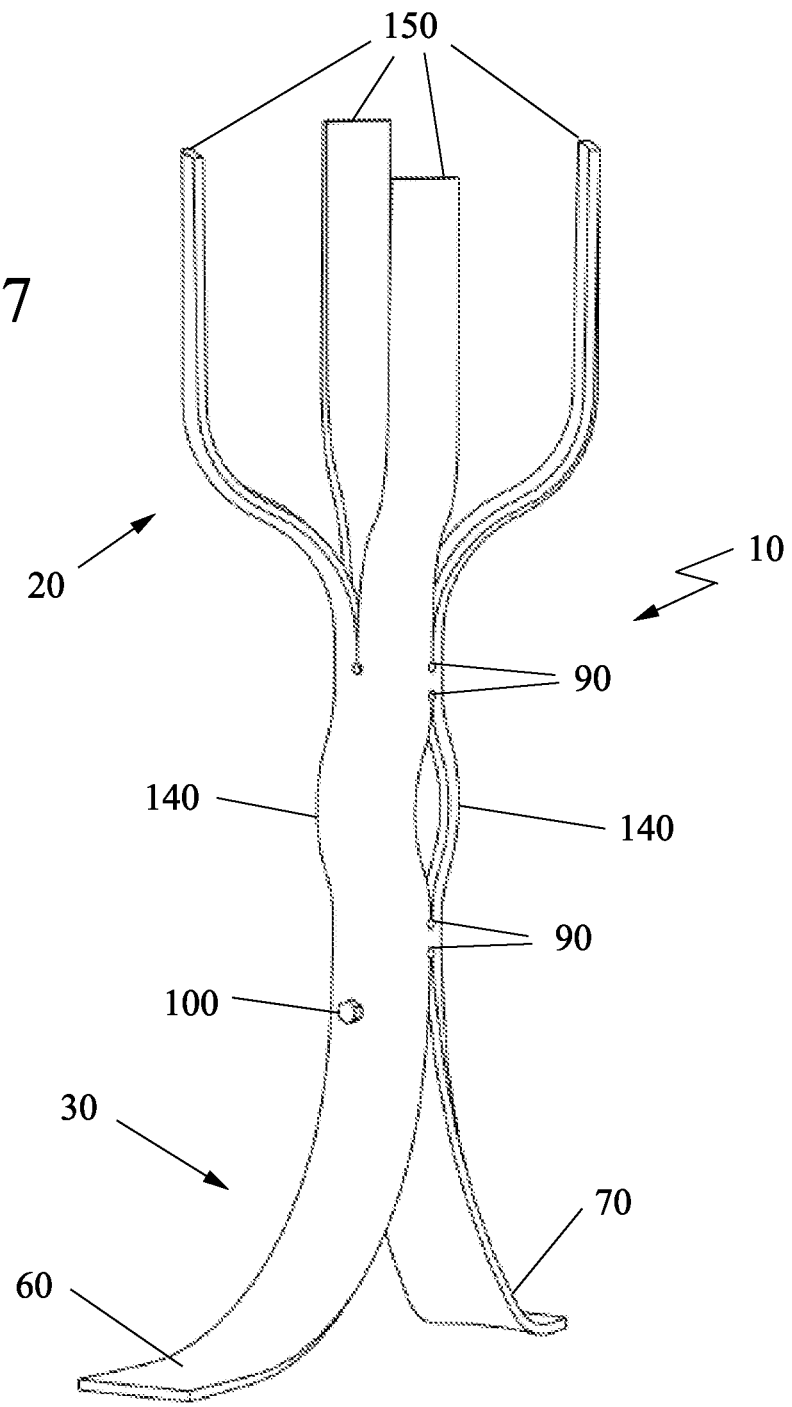
FIG. 7 illustrates a perspective view of an artificial limb of the present invention with fingers in an enlarged cup shape.
Figure 8:
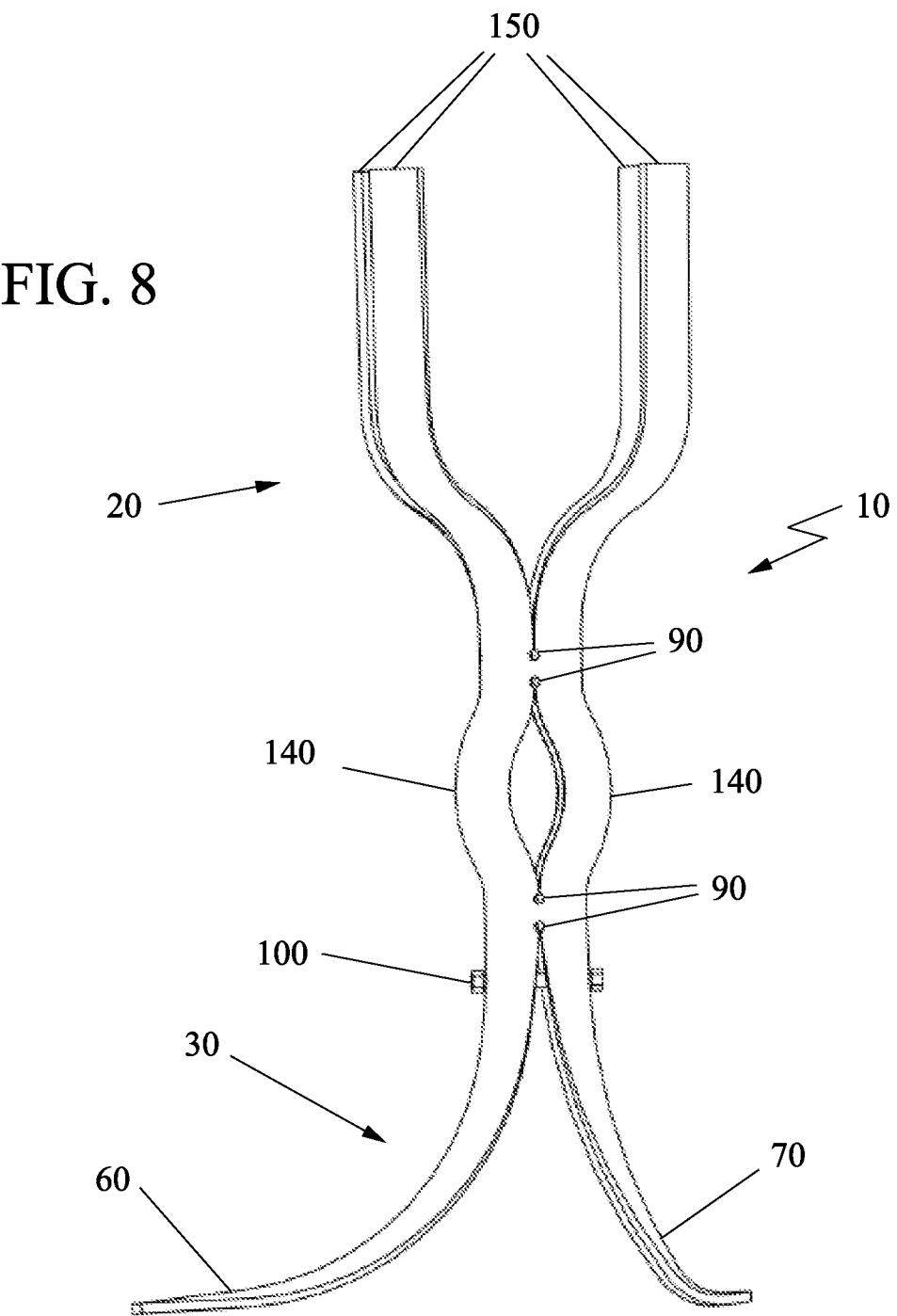
FIG. 8 illustrates a side plan view of an artificial limb of the present invention with fingers in an enlarged cup shape.

FIGS. 7 and 8 show an artificial limb with a plurality of circumferentially spaced-apart vanes 140. These vanes 140 are formed by dividing a portion of the elongated shaft member 10 between the proximal and distal ends 20 and 30 in a longitudinal direction and shaping the resulting divisions in the shaft member to a desired geometry. One purpose of creating the vanes 140 is to provide shock absorption and restorative force to the limb because the vanes 140 can elastically flex outward from the longitudinal axis of the elongated shaft member 10 and then spring back into their predefined shape when a longitudinal load is applied and removed from the limb. Another purpose of the vanes 140 is to provide additional rotational flexure to the limb, since the division of the midsection of the elongated shaft member 10 allows the distal end 30 and proximal end 20 of the limb to rotate more independently. The vanes 140 in that case also assist in rotating the proximal and distal ends of the limb back into their original alignment by storing energy during the rotation of the ends 20 and 30. The vanes 140 may also be augmented by attaching a bolt (not pictured) through the vanes near the terminus of the division between the vanes or by incorporating a hole 90 at the terminus of the divisions to reduce stresses generated when the vanes 140 flex. The dividing and shaping steps implemented in forming the vanes 140 are performed using techniques discussed elsewhere in this patent for dividing and shaping other parts of these artificial limbs.

In some embodiments, such as in FIGS. 7 and 8, an artificial limb with a plurality of circumferentially spaced-apart fingers 150 is implemented. To create this type of limb, the proximal end 20 of an elongated shaft member 10 is divided along circumferentially spaced sections to create fingers 150. The fingers 150 are also shaped into an enlarged cup shape with dimensions based on the size of the amputee's limb and to provide a suitable socket for a residual limb or other apparatus attached to the amputee's residual limb. The number of fingers 150 may increase or decrease due to these considerations, and the number of fingers 150 may also increase or decrease based on the strength of the material used in the elongated shaft member 10. The base of the divisions of the fingers 150 may beneficially have stress relief holes 90 or bolts (not pictured) added to minimize stress concentrations in the shaft when the fingers 150 flex. The dividing and shaping steps implemented in forming the fingers 150 are performed using techniques discussed elsewhere in this patent for dividing and shaping other parts of these artificial limbs.

Figure 9:
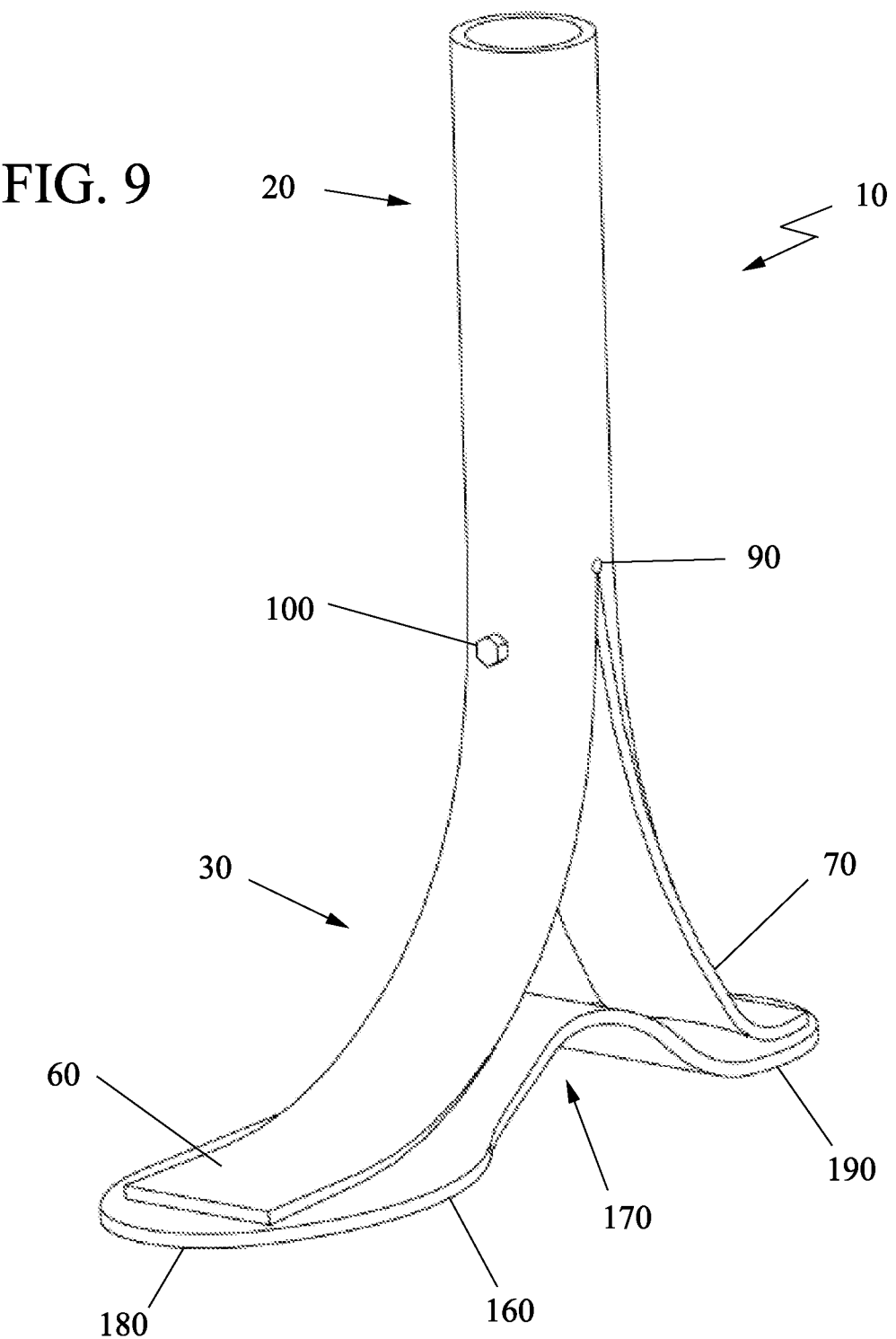
FIG. 9 illustrates a perspective view of an artificial limb of the present invention with a sole plate attached.
Figure 10:
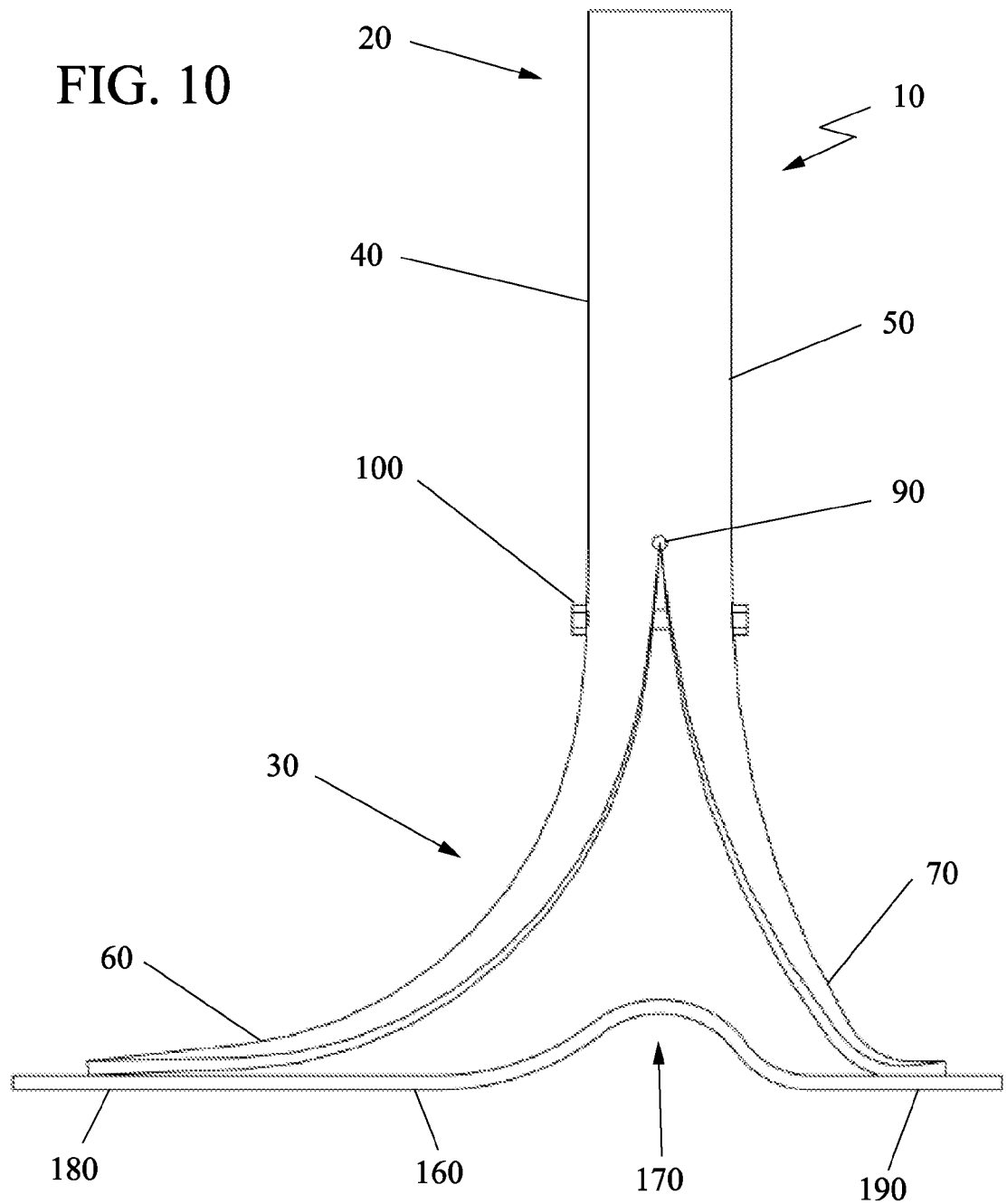
FIG. 10 illustrates a side plan view of an artificial limb of the present invention with a sole plate attached.

In FIGS. 9 and 10, an artificial limb with a sole plate 160 is depicted. The sole plate 160 in such embodiments is affixed to the prongs 60 and 70 on the distal end 30 of the elongated shaft member 10. The sole plate 160 may be formed with an arch 170 or other curves to provide stability and more natural foot shape to the wearer, and the anterior end 180 and posterior end 190 of the sole plate 160 may be beneficially shaped to custom fit a shoe or other additional apparatus. The affixing step may be performed using solvents, welding, mechanical fasteners, adhesives, and other similar strong connecting means, but it may also be performed by shaping the anterior and posterior ends 180 and 190 around the anterior and posterior prongs 60 and 70 to keep the sole plate 160 connected by mechanical interference of the parts. This can allow a user to interchange a variety of sole plates, such as interchanging plates of varying thicknesses. Users may thereby be enabled to participate in a greater variety of gait patterns that require a variety of mechanical stiffnesses in the foot. Additionally, the sole plate 160 may be affixed to prongs 60, 70, 110, and 120 of a reinforced limb (not pictured) or other limb described or claimed herein. The sole plate 160 may also be solely affixed at either the anterior end 180 or the posterior end 190 in these limbs instead of being affixed to both ends.

Figure 11:
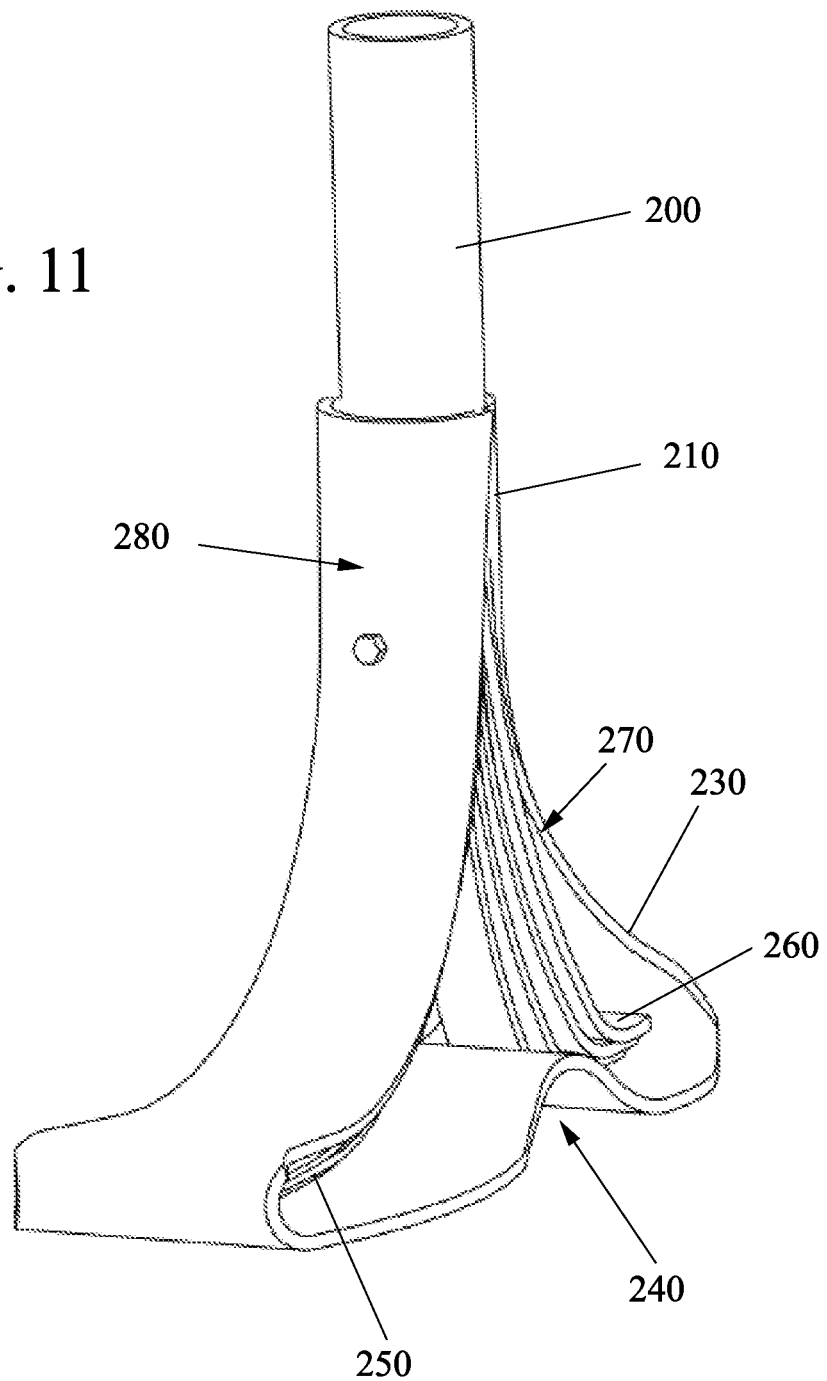
FIG. 11 illustrates a perspective view of an artificial limb of the present invention with a wrap-around design.
Figure 12:
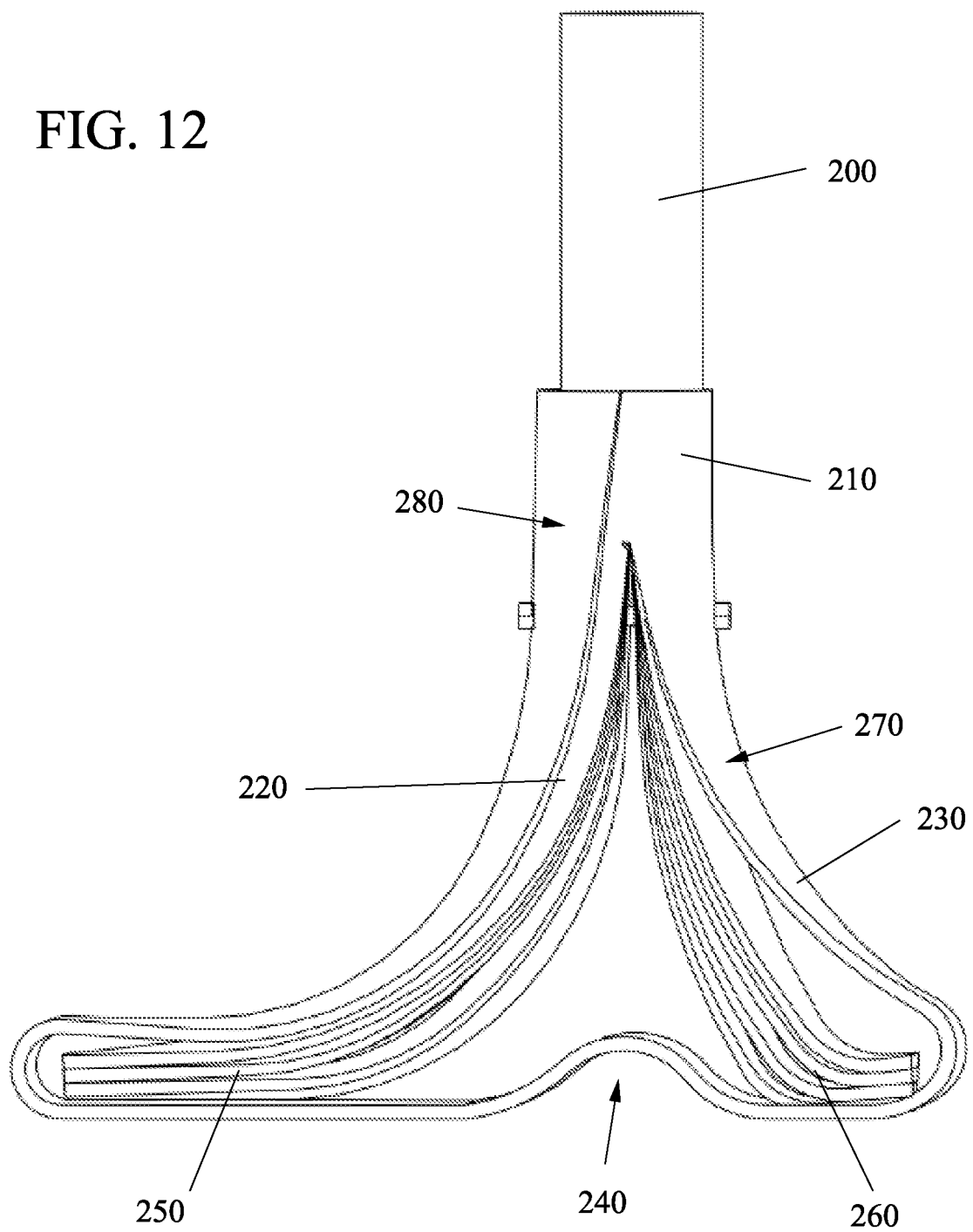
FIG. 12 illustrates a side plan view of an artificial limb of the present invention with a wrap-around design.

In some embodiments, a wrap-around foot design is implemented. FIGS. 11 and 12 show how this design may be implemented by taking an artificial limb 200 and augmenting it with an outer elongated shaft member 210 that is divided at its distal end into an anterior prong 220 and an elongated posterior prong 230. The artificial limb 200 is positioned within the outer elongated shaft member 210 so that the anterior prong or prongs 250 of the artificial limb 200 are aligned with the anterior prong 220. The posterior prong or prongs 260 of the artificial limb 200 are aligned with the proximal portion 270 of the elongated posterior prong 230. The distal portion 280 of the elongated posterior prong 230 is then shaped around the posterior prong or prongs 260 and the anterior prong or prongs 250 of the artificial limb 200 and attached to the anterior prong 220 of the outer elongated shaft member 210. An arch or division 240 in the outer elongated shaft member 230 may be added if the user desires. This attachment may be accomplished by a bolt or other techniques discussed elsewhere in this patent. Some advantages to using this design include increased durability, more customizable heel and toe sections, and increased stiffness.

The wrap-around foot design may also forego wrapping the outer elongated shaft member around another artificial limb design and may simply shape an anterior prong and elongated posterior prong in the way described above, but without shaping around another interior limb. In those embodiments, the outer elongated shaft member is itself attached to the limb or attachment apparatus of the amputee. This design reduces weight and may allow more varied toe and heel geometries.

The wrap-around design may also be modified by elongating the anterior prong rather than the posterior prong of the outer elongated shaft member 210 and wrapping the elongated anterior prong around the posterior prong.

Figure 13:
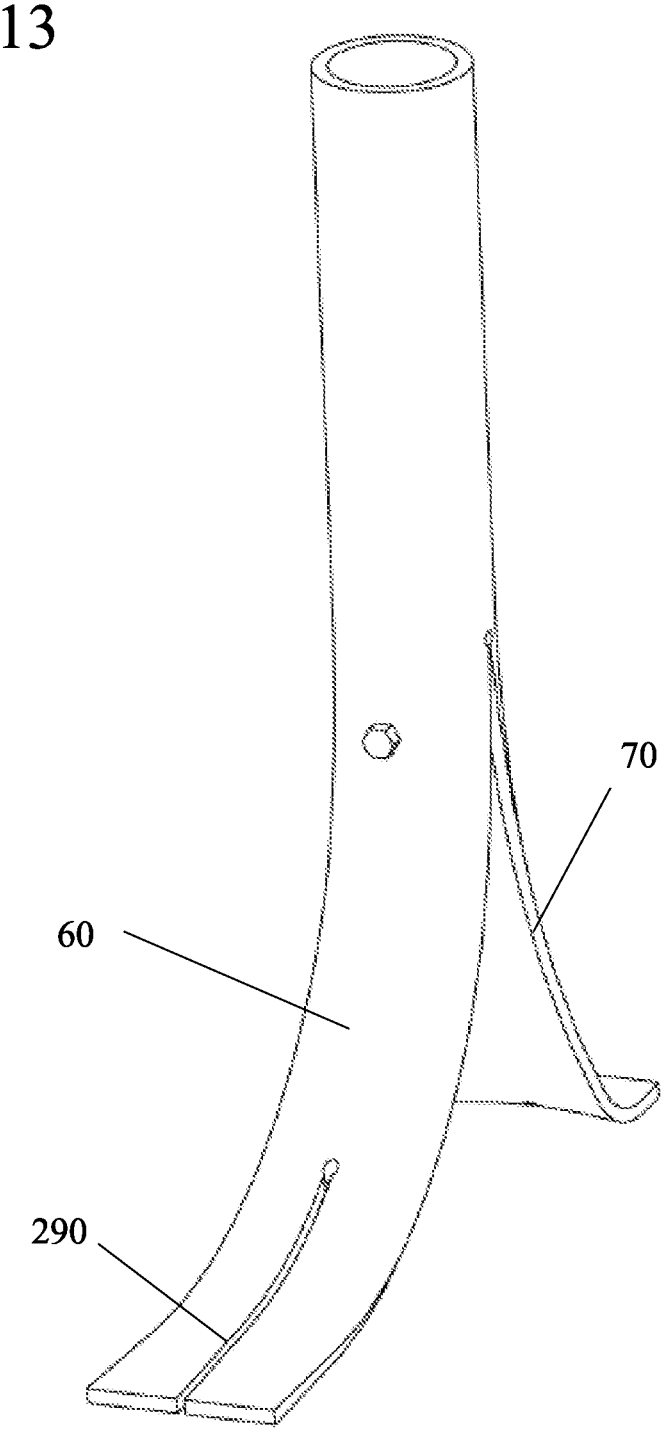
FIG. 13 illustrates an anterior perspective view of an artificial limb of the present invention with a plurality of toe extensions and heel extensions.
Figure 14:
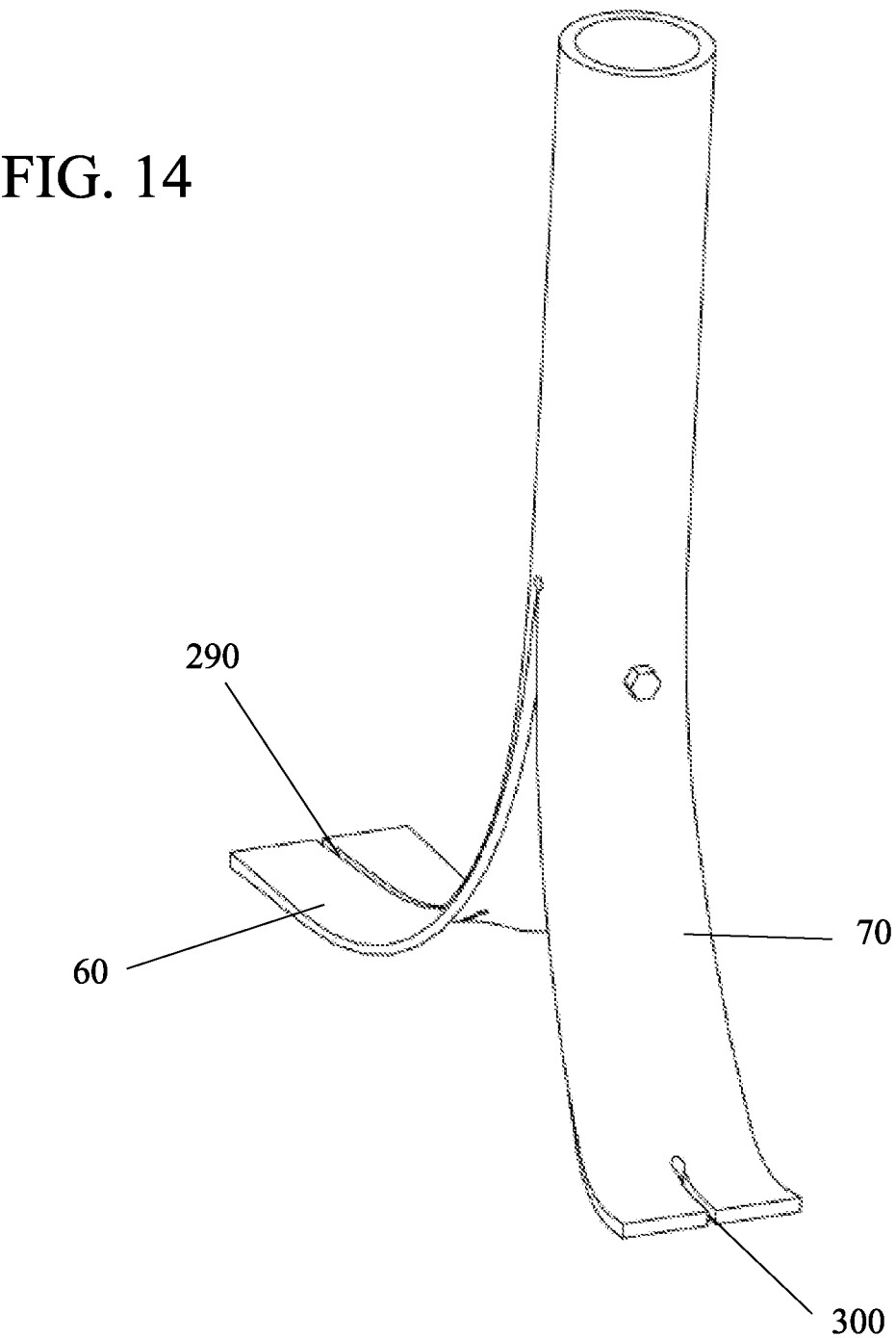
FIG. 14 illustrates a posterior perspective view of an artificial limb of the present invention with a plurality of toe extensions and heel extensions.

FIGS. 13 and 14 show that the anterior prong 60 and posterior prong 70 may also be divided into a plurality of extensions by slits 290 and 300. The anterior prong divisions, or toe extensions, and posterior prong divisions, or heel extensions, are independently flexible with respect to the remainder of the artificial limb, providing more natural bending to the ends of the prongs 60 and 70 if the limb rolls medially or laterally while under load. The number of toe and heel extensions, and the length of the slits 290 and 300 in the prongs 60 and 70, may increase or decrease depending on the needs of the wearer and the strengths and weaknesses of the material used in the prongs 60 and 70. Furthermore, reinforced prongs 60, 70, 110, and 120 and other designs described herein may be divided into a plurality of toe and heel extensions to suit the wearer's needs (not pictured). Stress relief holes may also be beneficially drilled to reduce stress concentration in the slits 290 and 300.

Combinations of the above mentioned embodiments should also be included within the scope of the present invention as described. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for making an artificial limb for attachment to a residual limb of an amputee from an elongated shaft member having a proximal end and a distal end along a longitudinal axis, comprising the steps of:

dividing an anterior side of said distal end of said shaft member from a posterior side of said distal end of said shaft member to form an anterior prong extending in an anterior direction from said longitudinal axis and to form a posterior prong extending in a posterior direction from said longitudinal axis;

shaping said anterior prong to a length and curvature based on the size and features of said amputee; and shaping said posterior prong to a length and curvature based on the size and features of said amputee.

2. The method according to claim 1, in which said elongated shaft member is a tubular member.

3. The method according to claim 2, in which said elongated shaft member is made of plastic.

4. The method according to claim 2, in which said elongated shaft member is made of fibrous composite.

5. The method according to claim 1, in which said shaping of said anterior prong and said shaping of said posterior prong is produced by cutting and molding said anterior prong and said posterior prong after heating said anterior prong and said posterior prong.

6. The method according to claim 1, further comprising:
dividing and shaping said proximal end of said shaft member to form a plurality of circumferentially spaced-apart fingers suitable for reception of said residual limb or an apparatus connected to said residual limb.

7. The method according to claim 1, further comprising:
dividing and shaping a portion of said shaft member disposed between said proximal end and said distal end of said elongated shaft member in a longitudinal direction to form a plurality of circumferentially spaced-apart vanes that flex in a direction perpendicular to said longitudinal axis when a longitudinal load is applied to said shaft member.

8. The method according to claim 1, further comprising:
attaching a bolt through said anterior prong and said posterior prong, wherein the attachment of said bolt limits the maximum movement of said anterior prong and said posterior prong when said prongs flex away from said longitudinal axis.

9. The method according to claim 1, wherein said anterior side and said posterior side of said distal end of said shaft member are divided by a slit in said shaft member, wherein said slit terminates in a hole through said shaft member of larger diameter than the width of said slit, said hole being capable of reducing the stress concentration in the hole end of said slit when said anterior prong and said posterior prong are drawn apart from each other.

10. The method according to claim 1, further comprising:
dividing said anterior prong into a plurality of toe extensions, said toe extensions being independently flexible with respect to the remainder of said artificial limb.

11. The method according to claim 1, further comprising:
dividing said posterior prong into a plurality of heel extensions, said heel extensions being independently flexible with respect to the remainder of said artificial limb.

12. The method according to claim 1, further comprising:
affixing a sole plate to said anterior prong.

13. The method according to claim 1, further comprising:
affixing a sole plate to said posterior prong.

14. The method according to claim 1, further comprising:
reinforcing said anterior prong and said posterior prong by dividing a distal end of an additional elongated shaft member into an additional anterior prong and an additional posterior prong and attaching said additional elongated shaft member to said distal end of said elongated shaft member such that said prongs and said additional prongs are nested to create a reinforced anterior prong and a reinforced posterior prong.

15. A method for making an artificial limb for attachment to a residual limb of an amputee from an outer elongated shaft member having a proximal end and a distal end along an outer longitudinal axis and an inner elongated shaft member having a proximal end and a distal end along an inner longitudinal axis, comprising the steps of:

dividing an anterior side of said distal end of said inner elongated shaft member from a posterior side of said distal end of said inner elongated shaft member;

shaping said anterior side into an inner anterior prong extending in an anterior direction from said inner longitudinal axis and said posterior side into an inner posterior prong extending in a posterior direction from said inner longitudinal axis;

dividing an anterior side of said distal end of said outer elongated shaft member from a posterior side of said distal end of said shaft member to form an outer anterior prong and an outer posterior prong;

nesting said inner elongated shaft member and said outer elongated shaft member such that said anterior side of said inner elongated shaft member and said anterior side of said outer elongated shaft member are aligned; and shaping said outer prongs to distally wrap around said inner prongs.

* * * * *